United States Patent
Liu et al.

(10) Patent No.: US 7,468,392 B1
(45) Date of Patent: Dec. 23, 2008

(54) ANTI-FATIGUE CYCLOHEXENONE COMPOUNDS FROM ANTRODIA CAMPHORATA

(75) Inventors: Sheng-Yun Liu, Taipei Hsien (TW); Mao-Tien Kuo, Taipei Hsien (TW); Wu-Che Wen, Taipei Hsien (TW)

(73) Assignee: Golden Biotechnology Corporation, Taipei Hsein (TW)

( * ) Notice: Subject to any disclaimer, the term of this patent is extended or adjusted under 35 U.S.C. 154(b) by 57 days.

(21) Appl. No.: 11/829,745

(22) Filed: Jul. 27, 2007

(30) Foreign Application Priority Data

Jun. 14, 2007 (TW) ............... 96121549 A (51) Int. Cl.
*A61K 31/12* (2006.01)
*C07C 49/543* (2006.01)

(52) U.S. Cl. ..................... 514/690; 568/377
(58) Field of Classification Search ........ None
See application file for complete search history.

(56) References Cited

OTHER PUBLICATIONS

Chen et al, "New Steroid Acids From *Antrodia cinnamomea*, A Fungal Parasite of Cinnamomum Micranthum", vol. 58, No. 11, pp. 1655-1661, Nov. 1995.
Cherng et al, "Three New Triterpenoids from *Antrodia cinnamomea*". vol. 58, No. 3, pp. 365-371, Mar. 1995.
Cherng et al, "Triterpenoids from *Antrodia cinnamomea*". vol. 41, No. 1, pp. 263-267, 1996.
Chiang et al. "A Sesquiterpene Lactone, Phenyl and Biphenyl Compounds from *Antrodia cinnamomea*". vol. 39, No. 3, pp. 613-616, 1995.
Yang et al. "Steroids and Triterpenoids of *Antrodia cinnamomea*-A Fungus Parasitic on Cinnamomum Micranthum". vol. 41, No. 5, pp. 1389 1392, 1996.

*Primary Examiner*—Sikarl A Witherspoon
(74) *Attorney, Agent, or Firm*—Birch, Stewart, Kolasch & Birch, LLP (57) ABSTRACT

The present invention relates to a compound of Antrodia camphorata used to delay physiological fatigue, in particular to a extract isolated from Antrodia camphorata, 4-hydroxy-2,3-dimethoxy-6-methyl-5(3,7,11-trimethyl-dodeca-2,6-10-trienyl)-cyclohex-2-enone, and its use in delaying fatigue. Immediate supplementation of the compound according to the invention after high intensity exhausted exercise at 80% $VO_2$max can promote the metabolism of creatine phosphate kinase and blood ammonia in human bodies, be beneficial to their recovery, further achieves the function in delaying physiological fatigue.

14 Claims, 5 Drawing Sheets

ANTI-FATIGUE CYCLOHEXENONE COMPOUNDS FROM ANTRODIA CAMPHORATA

BACKGROUND OF THE INVENTION

1. Field of the Invention

The present invention relates to an anti-fatigue compound, in particular to a cyclohexenone compound isolated and purified from *Antrodia camphorata* extracts

2. The Prior Arts

*Antrodia camphorata* is also called Chang-Zhi, Niu Chang-Zhi, red camphor mushroom and so on, which is a perennial mushroom belonging to the order Aphyllophorales, the family Polyporaceae. It is an endemic species in Taiwan growing on the inner rotten heart wood wall of *Cinnamomum kanehirai* Hay. *Cinnamoum kanehirai* Hay is rarely distributed and being overcut unlawfully, which makes *Antrodia camphorata* growing inside the tree in the wild become even rare. The price of *Antrodia camphorata* is very expensive due to the extremely slow growth rate of natural *Antrodia camphorata* that only grows between June to October.

The fruiting bodies of *Antrodia camphorata* are perennial, sessile, hard and woody, which exhales strong smell of sassafras (camphor aroma). The appearances are various with plate-like, bell-like, hoof-like, or tower-like shapes. They are reddish in color and flat when young, attached to the surface of wood. Then the brims of the front end become little curled tilted and extend to the surroundings. The color turns to be faded red-brown or cream yellow brown, with ostioles all over. It has very high medical value in this stage.

In traditional Taiwanese medicine, *Antrodia camphorata* is commonly used as an antidotal, liver protective, anti-cancer drug. *Antrodia camphorata*, like general edible and medicinal mushrooms, is rich in numerous nutrients including polysaccharides (such as β-glucosan), triterpenoids, superoxide dismutase (SOD), adenosine, proteins (immunoglobulins), vitamins (such as vitamin B, nicotinic acid), trace elements (such as calcium, phosphorus and germanium and so on), nucleic acid, agglutinin, amino acids, steroids, lignins and stabilizers for blood pressure (such as antodia acid) and the like. These physiologically active ingredients are believed to exhibit effects such as: anti-tumor activities, increasing immuno-modulating activities, anti-allergy, inhibiting platelet agglutination, anti-virus, anti-bacteria, anti-high blood pressure, decreasing blood sugar, decreasing cholesterol, hepatic protection, anti-fatigue function and the like.

Triterpenoids are the most studied component among the numerous compositions of *Antrodia camphorata*. Triterpenoids are the summary terms for natural compounds, which contain 30 carbon atoms with the pentacyclic or hexacyclic structures. The bitter taste of *Antrodia camphorata* is from the component of triterpenoids. Three novel ergostane-type triterpenoids (anticin A, anticin B, anticin C) were isolated by Cheng et al. from the fruiting bodies of *Antrodia camphorata* (Cherng, I. H., and Chiang, H. C. 1995. Three new triterpenoids from *Antrodia cinnamonea* J. Nat. Prod. 58:365-371). Three new compounds zhankuic acid A, zhankuic acid B and zhankuic acid were extracted from the fruiting bodies of *Antrodia camphorata* with ethanol by Chen et al. (Chen, C. H., and Yang, S. W. 1995. New steroid acids from *Antrodia cinnamomea*,—a fungus parasitic on *Cinnamomum mieranthum*. J. Nat. Prod. 58:1655-1661). In addition, Cherng, et al. also found three other new triterpenoids from the fruiting bodies of *Antrodia camphorata*, which are sesquiterpene lactone and 2 biphenyl derived compounds, 4,7-dimethoxy-5-methy-1,3-benzodioxole and 2,2',5,5'-teramethoxy-3,4,3',4'-bi-methylenedioxy-6,6'-dimethylbiphenyl (Chiang, H. C., Wu, D. P., Cherng, I. W., and Ueng, C. H. 1995. A sesquiterpene lactone, phenyl and biphenyl compounds from *Antrodia cinnamomea*. Phytochemistry. 39-613-616). In 1996, four novel ergostane-type triterpenoids (antcins E and F and methyl antcinates G and H) were isolated by Cherng et al. with the same analytic methods (Cherng, I. H., Wu, D. P., and Chiang, H. C. 1996. Triteroenoids from *Antrodia cinnamomea*. Phytochemistry. 41:263-267). And two ergostane related steroids, zhankuic acids D and E together with three lanosta related triterpenes, 15 alpha-acetyl-dehydrosulphurenic acid, dehydroeburicoic acid, dehydrosulphurenic acid were isolated by Yang et al. (Yang, S. W., Shen, Y. C., and Chen, C. H. 1996. Steroids and triterpenoids of *Antrodia cinnamomea*—a fungus parasite on *Cinnamomum microanthum*. Phytochemistry 41:1389-1392).

Searches for exact active ingredients are still in the experimental stage, and remain to be elucidated although the above-mentioned effects of *Antrodia camphorata* extracts were reported and the components were analyzed in succession. Among them, the anti-fatigue agent also needs further experiment to clarify. This will greatly contributes great beneficial effects on the studies for related mechanisms of *Antrodia camphorata* in anti-fatigue function and for the application in delaying fatigue for human bodies if the exact anti-fatigue composition is found.

SUMMARY OF THE INVENTION

In order to identify the anti-fatigue compounds from the extracts of *Antrodia camphorata*, the compound of the formula (1) was isolated and purified in this invention, wherein X and Y can be oxygen or sulfur, $R_1$, $R_2$ and $R_3$ are each a hydrogen atom, methyl or $(CH_2)_m$—$CH_3$ and m=1-12; n=1-12.

A preferred compound of the general formula (1) is 4-hydroxy-2, 3-dimethoxy-6-methyl-5 (3,7,11-trimethyl-dodeca-2, 6,10-trienyl)-cyclohex-2-enone as shown in formula (2), with molecular formula of $C_{24}H_{38}O_4$, appearance of pale yellow powder and molecular weight of 390.

Cyclohexenone compounds having the structures of formula (1) and formula (2) are purified from aqueous extraction or organic solvent extraction of *Antrodia camphorata*. The organic solvents used include, but not limited to, alcohols such as methanol, ethanol or propanol, esters such as ethyl acetate, alkanes such as hexane, or halogenated alkanes such as chloromethane, chloroethane. Among them, alcohol is preferred, and ethanol is particularly preferred.

The present invention tested the cyclohexenone compounds of the formula (1) and the formula (2) in delaying fatigue. Cyclohexenone of *Antrodia camphorata* was supplemented after a high-intensity exhaustive exercise at 80% $VO_2$max in order to facilitate creating phosphate kinase (CPK) and ammonia metabolism to return to baseline levels, to eliminate the muscle cell impairment due to exercise, to reduce central and peripheral fatigue associated with exercise due to the blood ammonia accumulation, and finally to achieve the anti-fatigue function.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

DETAILED DESCRIPTION OF THE PREFERRED EMBODIMENT

The mycelia, fruiting bodies or mixture of both from *Antrodia camphorata* are first extracted with water or organic solvents to obtain the aqueous extract or organic solvent extract of *Antrodia camphorata* using the methods well known in the arts. The organic solvents include, but are not limited to, alcohols such as methanol; ethanol or propanol; esters such as ethyl acetate; alkanes such as hexane; or halogenated alkanes such as chloromethane, and chloroethane. Among them, alcohol is preferred, and ethanol is particularly preferred.

The aqueous or organic solvent extracts of *Antrodia camphorate* were subjected to high-performance liquid chromatography (HPLC) for isolation and purification. Each fraction was recovered and assayed for anti-fatigue function. The potent fractions with anti-fatigue function were analyzed for the composition and further assayed with different anti-fatigue biochemical tests. The above approach then led to the identification compounds of the formula (1) and formula (2) of anti-fatigue function.

The compound 4-hydroxy-2,3-dimethoxy-6-methyl-5(3, 7,11-trimethyl-dodeca-2,6,10-trientyl)-cyclohex-2-enone of the formula (2) are explained below as an example for the present invention. The anti-fatigue function of the 4-hydroxy-2,3-dimethoxy-6-methyl-5(3,7,11-trimethyl-dodeca-2,6,10-trienyl)-cyclohex-2-enone was assessed by testing the fatigue indexes of CPK, lactic acid, glucose, ammonia and free fatty acid levels in plasma in the subjects after exhaustive exercising at 80% $VO_2$max. The above assays had proved that 4-hydroxy-2,3-dimethoxy-6-methyl-5(3,7,11-trimethyl-dodecca-2,6,10-trienyl)-cyclohex-2-enone can be used to delay physiological fatigue after exercise. The details of the examples are described as follows:

EXAMPLE 1

Isolation of 4-hydroxy-2,3-dimethoxy-6-methyl-5(3, 7,11-trimethyl-dodeca-2,6,10-trienyl)-cyclohex-2-enone 100 g of mycelia, fruiting bodies or mixture of both from *Antrodia camphorata* were placed into a flask. A proper amount of water and alcohol (70-100% alcohol solution) was added into the flask and were stirred at 20-25° C. for at least 1 hour. The solution was filtered through a filter and a 0.45 μm membrane and the filtrate was collected as the extract.

The filtrate of *Antrodia camphorata* was subjected to High Performance Liquid chromatography (HPLC) analysis. The separation was performed on a RP18 column, the mobile phase consisted of methanol (A) and 0.1-0.5% acetic acid (B), with the gradient conditions of 0-10 min in 95%-20% B, 10-20 min in 20%~10% B, 20-35 min in 10%-10% B, 35-40 min in 10%~95% B, at the flow rate of 1 ml/min. The column effluent was monitored with a UV-visible detector.

The fractions collected at 25-30 min were collected and concentrated to yield 4-hydroxy-2,3-dimethoxy-6-methyl-5 (3,7,11-trimethyl-dodeca-2,6,10-trienyl)-cyclohex-2-enone, a product of pale yellow powder. The analysis of 4-hydroxy-2,3-dimethoxy-6-methyl-5(3,7,11-trimethyl-dodeca-2,6,10-trienyl)-cyclohex-2-enone showed the molecular formula of $C_{24}H_{38}O_4$, molecular weight of 390, melting point of 48° C.~52° C. Investigation of NMR spectra showed that $^1$H-NMR($CDCl_3$)δ(ppm)=1.51, 1.67, 1.71, 1.75, 1.94, 2.03, 2.07, 2.22, 2.25, 3.68, 4.05, 5.07, and 5.14; $^{13}$C-NMR ($CDCl_3$)δ(ppm)=12.31, 16.1, 16.12, 17.67, 25.67, 26.44, 26.74, 27.00, 39.71, 39.81, 4.027, 43.34, 59.22, 60.59, 120.97, 123.84, 124.30, 131.32, 135.35, 135.92, 138.05, 160.45, and 197.12.

EXAMPLE 2

Test Of Exercise Load At 80% VO$_2$max

The anti-fatigue effect of supplementing cyclohexenone of *Antrodia camphorata* was tested after exhaustive exercising at 80% VO$_2$max. Maximum oxygen uptake was measured to figure out the speed at 80% VO$_2$max. Oxygen uptake is calculated from the product of cardiac output and the difference in oxygen concentration in the arterial and venous blood. While maximum oxygen uptake is the maximum capacity of cells in tissues to transport and utilize oxygen during most violent exercise for a subject above sea level, which is the best index for cardio-respiratory endurance. Direct measurement of maximal oxygen uptake capacity using a treadmill inside a lab was carried out in the present invention. A spirometer was directly used to calculate the maximal oxygen uptake during increment exercise to the maximum workload. This incremental continuous load exercise is able to induce the real maximal oxygen uptake capacity and therefore becomes the direct and accurate measuring method for maximal oxygen uptake.

(1) Basic Information Collection For Volunteers

A total of 15 healthy male volunteers (n=15) aged more than 20 years old were recruited as test subjects for the invention. All candidates were not taking drugs, with normal liver and kidney functions, had no cardiovascular disease, non-smoking, non-alcohol drinking, and no nutritional supplement-taking habit. The basic information includes age, height, body weight and BMI was recorded. No food or drink was taken 8 hours before the formal test. Normal diets were maintained but no other drugs or nutritional supplements were taking during study period to prevent the effects of experimental data.

(2) Test Of Exercise Load At 80% VO$_2$max

The formal maximal oxygen uptake VO$_2$max were tested after twice pretest in the subjects and estimated the exercise load at 80% VO$_2$max. The 80% VO$_2$max was tested again to confirm the exercise intensity was under the defined load of the subjects. The procedures were described in details below.

The spirometer Vmax Spectra (SensorMedics) was calibrated with standard oxygen and gases in different concentrations before the arrival of volunteers for maximal oxygen uptake measurement. The volunteers wore Polar 810i Heart rate monitor watch when arrived and the resting heart rates were recorded. The transmission belt was put close to the heart of each subject. The distance between the watch and the belt was within one meter. Subjects were familiarized with treadmill (Vision, T8600) running for 3-5 min, and executed stretching exercises by themselves. Each subject wore a gas-sampling mask when stood in the treadmill, which was connected to a spirometer Vmax Spectra via a breathing tube. Expiratory gas was collected via this tube-connection into the spirometer Vmax Spectra. Throughout the test treadmill speed was held constant at 9.6 km/hr. Slope of the treadmill started from 0% and increased by 3% every 3 min until the subject was exhausted. Oxygen uptake was measured from the data of spirometer Vmax Spectra one min before the elevation and being exhausted. The maximal value of oxygen uptake in each test is the maximal oxygen uptake value. In addition, the maximal oxygen uptake has to fulfill two of the following criteria: (a) subject was no longer able to continuous exercise (the running pace of subject could not follow the treadmill belt); (b) heart rate reached (220−age)±10 per min; (c) respiratory quotient (RQ) was larger than 1.1; (d) rating perceived exertion (RPE) reached 18 or 19.

The velocity at 80% VO$_2$max could be obtained by regression analysis of measured maximal oxygen uptake and loading intensity. The calculation was carried out with the data of oxygen uptake and velocity from previous test, where a regression line was obtained from velocity (vertical axis) and oxygen uptake (horizontal axis). The maximal oxygen uptake of each subject was multiplied by 80% to obtain 80% VO$_2$max and the corresponding velocity was found through the regression line. This loading intensity (velocity) was exercised for 10 min, and the oxygen uptake at the 5-6 min and the last 1 min was measured to ascertain the real exercise load at 80% VO$_2$max. The result is shown in Table 1.

TABLE 1

Basic information of the volunteers and their maximal oxygen uptake

| Items | Data (mean ± standard error) |
|---|---|
| age | 22.8 ± 0.89 |
| height (m) | 1.75 ± 0.01 |
| weight (kg) | 67.73 ± 1.81 |
| BMI (kg × m$^{-2}$) | 22.14 ± 0.63 |
| maximal oxygen uptake (ml/min/kg) | 50.22 ± 0.17 |
| 80% maximal oxygen uptake velocity | 7.61 ± 1.87 | n = 15

EXAMPLE 3

Anti-Fatigue Test For Cyclohexenone Of *Antrodia camphorata*

A broad applied definition of fatigue during exercise is that the physiology of a subject can not function in normal abilities or the organs in the body are not able to maintain the same intensity for exercise. The reasons for fatigue during activities include psychological, physiological and biochemical factors. Among them, the potent mechanism for biochemical fatigue has two components, central and peripheral. Mechanisms of central fatigue can be caused by hypoglycemia, the changes of critical amino acid concentrations in blood as well as the changes of concentrations of neural transmitting substances in brain. Mechanisms implicated in peripheral fatigue include blood ammonia addition due to the lack of phosphocreatine (PC) in muscle, shortage of energy source due to depletion of muscle glycogen, oxygen and the like, lactic acid addition caused by hydrogen ion accumulation, accumulation of phosphoric acid and other metabolic by-products.

The present invention is based on supplementing cyclohexenone of *Antrodia camphorata* or placebo with no cyclohexenone of *Antrodia camphorata* to the subjects. The subjects were tested for the anti-fatigue function after supplementing cyclohexenone of *Antrodia camphorata* by measuring the amounts of fatigue indexes such as CPK, lactic acid, glucose, ammonia and free fatty acid before and after exhaustive exercise load at 80% VO$_2$max.

Subjects were randomized to receive either cyclohexenone of *Antrodia camphorata* or placebo. Placebo contained substances such as cornstarch but no cyclohexenone of *Antrodia* camphorata. A double-blind, cross-over method was performed in this study where neither the evaluator nor the subject knew the content of the test substances. Based on rules of order balance, each subject have to receive the following tests: relaxing and receiving placebo (PR), exercising and receiving placebo (PE), relaxing and receiving cyclohexenone of Antrodia camphorata (DR), and exercising and receiving cyclohexenone of Antrodia camphorata (DE). Each test was carried out for one week, and took one week off before the next test until all 4 tests were performed in each subject. The exercise was performed on a treadmill with the load intensity at the measured 80% $VO_2$max (7.61±1.87) until exhausted. Subjects received cyclohexenone of Antrodia camphorata or placebo after exercise in the amount of 0.2 g/kg body weight per day. Subjects had a venous blood sample drawn before the exercise and 0, 0.5, 1, 2, 24, 48, 72, 120 and 168 h after the exercise. Blood was collected in anticoagulant (such as EDTA) containing collection tubes, and was centrifuged at 3000 g. for 10 min to collect the plasma. The fatigue indexes such as CPK, lactic acid, glucose, ammonia and free fatty acid were analyzed accordingly. The physiological and biochemical changes before and after exercise with different supplements were compared and shown as values of mean and standard error (Mean±SEM). These values were analyzed using repeated measurement two way, ANOVA in different sampling points between groups and within groups with the post hoc analyses by Tukey's honestly significant difference test ($\alpha$=0.05). The details for the biochemical analysis and results are described below:

(1) Creatine Phosphate Kinase (CPK) Activity

Serum creatine phosphate kinase is present in human organs such as skeletal muscle, heart muscle, brain, prostate gland, and the like, which is most abundant in skeletal muscle (96% of whole body). CPK activity is low under normal condition, which catalyzes the reaction of the transfer phosphate from phosphate creatine to ADP to form ATP to rapidly provide the energy needed and promote ATP formation during exercise for muscle contraction. The reaction is:

$$ADP + PC \xrightarrow{CPK} ATP + creatine$$

The reason for CPK activity's increase is due to lack of oxygen during exercise, which caused accumulation of metabolic products and impaired calcium ion balance inside and outside of cells. The permeability of muscle cell membrane is increased or muscle cell membrane is damaged associated with mechanical injury for muscular strain or formation of hematoma; hence the creatine phosphate kinase is released into blood stream. CPK is therefore used as an enzyme marker for exercise intensity and muscle cell damage.

The measurement of creatine phosphate kinase was performed with an automated blood analyzer Johnson & Johnson DT-60II based on enzyme function and spectrophotometric theory. Creatine phosphate glucose oxidase was added into a defined amount of plasma to react, followed by addition of 4-aminoantipyrine and 1,7-dihydroxynaphthalene. A white product was formed through peroxidase function. The absorbance at 680 nm was measured to obtain the concentration of creatine kinase. Results are shown in Table 2 and FIG. 1.

TABLE 2

The creatine phosphate kinase levels (U/L) of the subjects supplemented with placebo or cyclohexenone of Antrodia camphorata before or after exercise.

| Group | Prior to exercise | Post-exercise 0 h | Post-exercise 0.5 h | Post-exercise 1 h | Post-exercise 2 h | Post-exercise 24 h | Post-exercise 48 h | Post-exercise 72 h | Post-exercise 120 h | Post-exercise 168 h |
|---|---|---|---|---|---|---|---|---|---|---|
| Placebo | | | | | | | | | | |
| Relax (PR) | 205.40 ± 42.49 | 204.80 ± 40.28 | 206.27 ± 40.54 | 198.33 ± 42.99 | 194.67 ± 40.77 | 179.73 ± 25.81 | 148.13 ± 18.00 | 194.07 ± 25.92 | 193.40 ± 22.44 | 171.73 ± 22.75 |
| exercise (PE) | 152.00 ± 32.06 | 232.13 ± 38.98*[ac] | 219.20 ± 33.56*[acd] | 295.33 ± 29.88*[acd] | 188.47 ± 32.25*[c] | 383.53 ± 134.86[c] | 321.60 ± 99.33[ac] | 360.20 ± 111.71[acd] | 279.73 ± 69.06 | 231.13 ± 70.20 |
| cyclohexenone | | | | | | | | | | |
| Relax (DR) | 167.27 ± 19.5 | 150.20 ± 21.71* | 166.53 ± 19.71 | 167.40 ± 23.16 | 146.33 ± 23.16 | 158.47 ± 21.63 | 133.87 ± 16.51 | 165.73 ± 28.08 | 243.00 ± 48.21 | 183.27 ± 38.37 |
| exercise (DE) | 226.64 ± 37.20 | 259.57 ± 38.83*[c] | 221.86 ± 37.74 | 232.93 ± 32.98 | 208.07 ± 30.53 | 332.50 ± 81.75 | 244.00 ± 49.65 | 193.86 ± 34.44 | 193.86 ± 25.49 | 204.83 ± 31.89 | n = 15, values are presented as (Mean ± SEM).
*represents p < .05, significant difference from the previous test;
[a]represents p < .05, significant larger than that of the same time point in the PR group;
[b]represents p < .05, significant higher than that of the same time point in the PE group;
[c]represents p < .05, significant higher than that of the same time point in the DR group;
[d]represents p < .05, significant higher than that of the same time point in the DE group.

Figure 1:
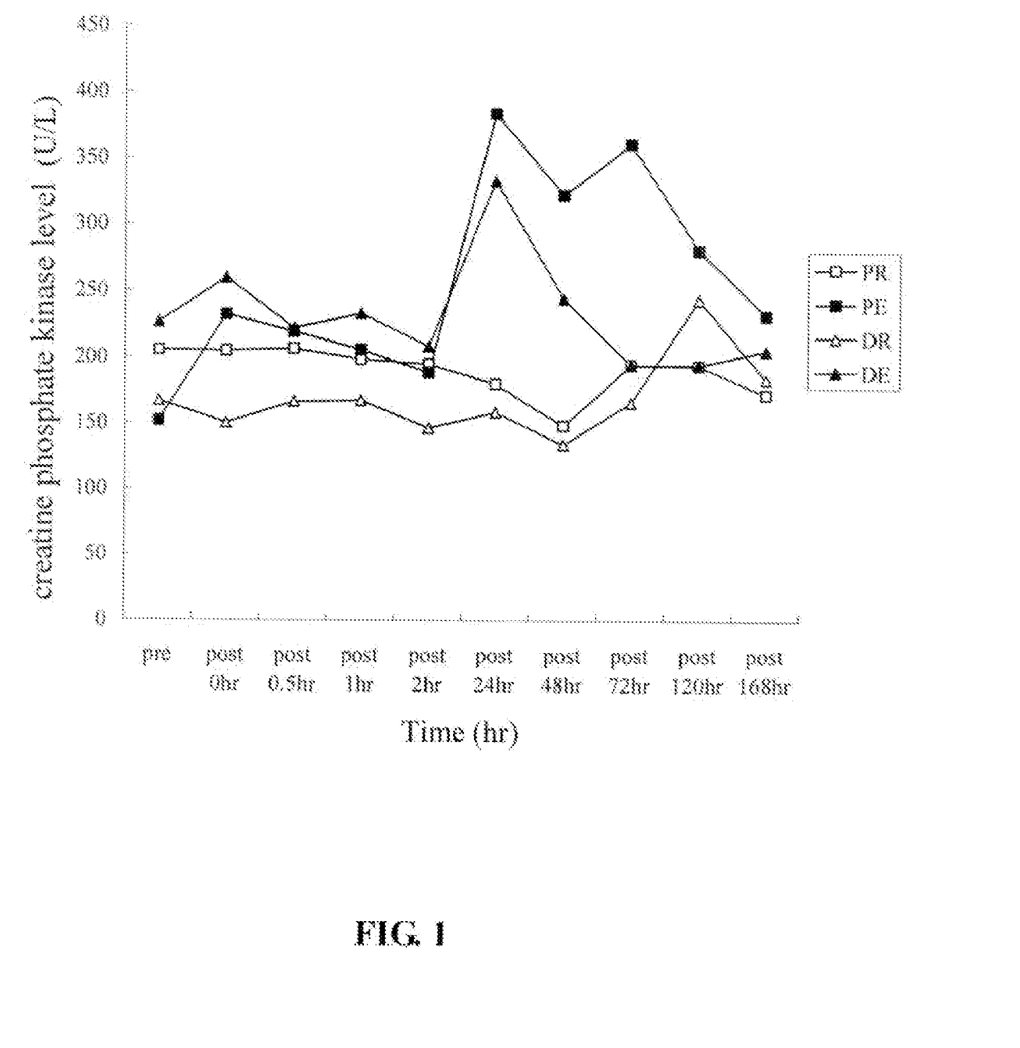
FIG. 1. The creatine phosphate kinase levels in each time point of the subjects supplemented with placebo or cyclohexenone of *Antrodia camphorata* before or after exercise. □: The relax group receiving placebo (PR), ▓ the exercise group receiving placebo (PE), Δ:the relax group receiving cyclohexenone of *Antrodia camphorata* (DR), ▲: the exercise group receiving cyclohexenone of *Antrodia camphorata* (DE).

From the results of Table 2 and FIG. 1, the creatine phosphate kinase levels of 0, 0.5, 1, 2, and 24 h post exercise were constantly increased and were significantly higher than those before exercise in PE group (the exercise group receiving placebo), which also suggested the exercise intensity of subjects had reached muscular injury. The creatine phosphate kinase levels of PE group were significantly higher than those of PR group (the relax group receiving placebo) and DR group (the relax group receiving cyclohexenone of Antrodia camphorata). Both the values of PR group and DR group showed no difference at 120 h post exercise.

The creatine phosphate kinase levels of DE group (the exercise group receiving cyclohexenone of Antrodia camphorata) increased right away after high intensity exhausted exercise, but recovered to the level before exercise after 0.5 h. In addition, creatine phosphate kinase levels of PE group after exhaustive exercise were significantly higher (p<0.05) than those of DE group, and this difference can be observed from the time of exercise to 1 h post exercise, as well as 72 h post exercise. Immediate supplementation of cyclohexenone from *Antrodia camphorata* after exercise therefore effectively decreases the muscular injury marker of creatine phosphate kinase levels, which is helpful in delaying the fatigue due to exercise.

(2) Blood Glucose Before Meals

Calcium ions and epinephrine were released due to muscle contraction during exercise to active phosphorylase. This is associated with an increase in blood lactate levels followed by glycogenolysis. Glycogen stored in muscle would be depleted during high intensity exhausted exercise at 80% $VO_2$max and followed by generation of fatigue. Therefore, blood glucose levels can be applied as an index for fatigue.

The measurement of blood glucose was performed with an automated blood analyzer Johnson & Johnson DT-600 II based on enzyme function and spectrophotometric method. Glucose oxidase was added into a defined amount of plasma for reaction, followed by addition of 4-aminoantipyrine and 1,7-dihydroxyphthalene. A red product was formed through function of peroxidase. The reactions are shown below:

The absorbance at 555 nm was measured to obtain the concentration of blood glucose. Results are shown in Table 3 and FIG. 2.

TABLE 3

The blood glucose levels (mg/dl) of the subjects supplemented with placebo or cyclohexenone of *Antrodia camphorata* before or after exercise.

| Group | Prior to exercise | Post-exercise 0 h | Post-exercise 0.5 h | Post-exercise 1 h | Post-exercise 2 h | Post-exercise 24 h | Post-exercise 48 h | Post-exercise 72 h | Post-exercise 120 h | Post-exercise 168 h |
|---|---|---|---|---|---|---|---|---|---|---|
| Placebo | | | | | | | | | | |
| Relax (PR) | 90.27 ± 1.80 | 90.73 ± 1.90 | 92.87 ± 2.62 | 92.27 ± 1.71 | 97.20 ± 4.84 | 86.87 ± 1.85 | 87.73 ± 1.65 | 90.20 ± 1.08 | 88.47 ± 0.90 | 87.47 ± 2.25 |
| exercise (PE) | 89.67 ± 2.50 | 106.60 ± 4.25*[ac] | 90.00 ± 3.34 | 97.73 ± 5.15 | 99.13 ± 5.90 | 92.47 ± 3.16[a] | 90.33 ± 2.11 | 91.47 ± 1.57 | 88.13 ± 1.90 | 91.07 ± 1.75 |
| cyclohexenone | | | | | | | | | | |
| Relax (DR) | 91.73 ± 1.65 | 91.93 ± 1.95 | 93.33 ± 2.99 | 95.53 ± 3.23 | 103.20 ± 4.35* | 90.00 ± 1.91 | 90.40 ± 2.56 | 93.40 ± 2.34 | 94.00 ± 2.65[ab] | 92.20 ± 1.98 |
| exercise (DE) | 89.21 ± 2.02 | 103.43 ± 4.49*[ac] | 88.71 ± 1.74 | 93.86 ± 2.03 | 101.07 ± 6.03* | 94.43 ± 1.57[ac] | 89.21 ± 1.69 | 93.00 ± 1.42 | 93.29 ± 1.42[b] | 92.93 ± 1.34[a] | n = 15, values are presented as (Mean ± SEM).

*represents p < .05, significant difference from the previous test;

[a]represents p < .05, significant larger than that of the same time point in the PR group;

[b]represents p < .05, significant higher than that of the same time point in the PE group;

[c]represents p < .05, significant higher than that of the same time point in the DR group;

[d]represents p < .05, significant higher than that of the same time point in the DE group.

Figure 2:
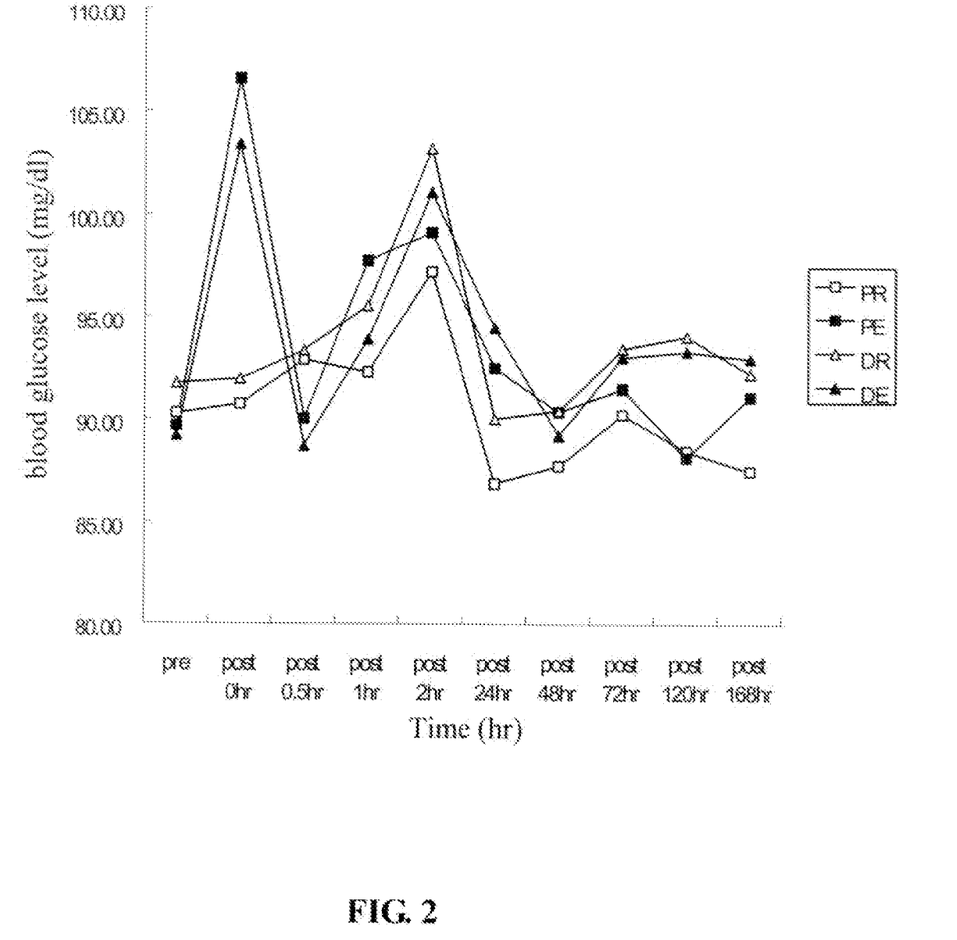
FIG. 2. The blood glucose levels in each time point of the subjects supplemented with placebo or cyclohexenone of *Antrodia camphorata* before or after exercise. □: the relax group receiving placebo (PR), ▓ the exercise group receiving placebo (PE), Δ: the relax group receiving cyclohexenone of *Antrodia camphorata* (DR). ▲: the exercise group receiving cyclohexenone of *Antrodia camphorata* (DE).

From the results of Table 3 and FIG. 2, the blood glucose levels in the PE group and the DE group after high intensity exhausted exercise at 80% VO$_2$max were significantly different from those in the PR group and in the DR group ($p<0.05$). The blood glucose levels before meal of PE group and DE group at 0.5 h after high intensity exhausted exercise at 80% VO$_2$max would recover to the level before exercise and near the quiet values. The supplementation of cyclohexenone from *Antrodia camphorata* showed no effect to the blood glucose metabolism before meals.

(3) Analysis Of Ammonia Levels In Blood

Blood ammonia is the metabolic product of protein, which is contributed by amino acid degradation in purine nucleotide cycle (PNC) and deamination of adenosine monophosphate (AMP). Adeninenucleotde in tissue was degraded due to the depletion of creatine phosphate during exercise to promote re-synthesis of ATP. Ammonia level will be increased to a large extent. And when excessive ammonia is produced, which results in changes of pH, electrolytes concentration and the concentration of neural transmitting substance by central nervous system disorders. Fatigue was initiated by interference of Krebs cycle. Accumulation of ammonia is one of the factors to cause central fatigue and peripheral fatigue. Ammonia is therefore used as an index for fatigue.

The measurement of blood ammonia was performed with an automated blood analyzer Johnson & Johnson DT-60II based on the spectrophotometric method. Bromphenol blue was added into a defined amount of plasma to generate blue products. The reaction is shown below:

NH$_3$ + Bromphenol blue ⟶ Blue dye

The absorbance at 605 nm was measured to obtain the concentration of blood ammonia. Results are shown in Table 4 and FIG. 3.

TABLE 4

The blood ammonia levels (μg/dl) of the subjects supplemented with placebo or cyclohexenone of *Antrodia camphorata* before or after excercise.

| Group | Prior to exercise | Post-exercise 0 h | Post-exercise 0.5 h | Post-exercise 1 h | Post-exercise 2 h | Post-exercise 24 h | Post-exercise 48 h | Post-exercise 72 h | Post-exercise 120 h | Post-exercise 168 h |
|---|---|---|---|---|---|---|---|---|---|---|
| Placebo | | | | | | | | | | |
| Relax (PR) | 49.93 ± 5.71 | 61.67 ± 7.61* | 64.53 ± 4.68* | 74.00 ± 6.55*[d] | 69.07 ± 8.37*[d] | 39.27 ± 4.0 | 28.73 ± 3.15* | 30.73 ± 4.94* | 21.27 ± 2.86* | 32.14 ± 3.22* |
| exercise (PE) | 52.73 ± 4.40 | 153.27 ± 16.38*[ac] | 75.27 ± 5.42* | 64.40 ± 5.85 | 73.20 ± 10.49[d] | 40.27 ± 6.01 | 27.73 ± 3.28* | 27.43 ± 2.92* | 24.71 ± 3.63* | 29.60 ± 3.53* |
| cyclohexenone | | | | | | | | | | |
| Relax (DR) | 39.20 ± 6.87 | 55.60 ± 9.72 | 52.53 ± 8.16 | 57.47 ± 7.83* | 54.07 ± 7.05 | 30.33 ± 4.51 | 26.86 ± 2.48 | 25.20 ± *4.45 | 27.80 ± 4.63* | 28.57 ± 3.61 |
| exercise (DE) | 45.86 ± 7.28 | 118.07 ± 11.06*[ac] | 57.64 ± 7.96* | 44.86 ± 7.23 | 37.53 ± 6.09 | 27.93 ± 2.96* | 20.93 ± 2.28* | 30.07 ± 5.56* | 23.21 ± 2.28* | 24.86 ± 4.04* | n = 15, values are presented as (Mean ± SEM).

*represents p < .05, significant difference from the previous test;

[a]represents p < .05, significant larger than that of the same time point in the PR group;

[b]represents p < .05, significant higher than that of the same time point in the PE group;

[c]represents p < .05, significant higher than that of the same time point in the DR group;

[d]represents p < .05, significant higher than that of the same time point in the DE group.

Figure 3:
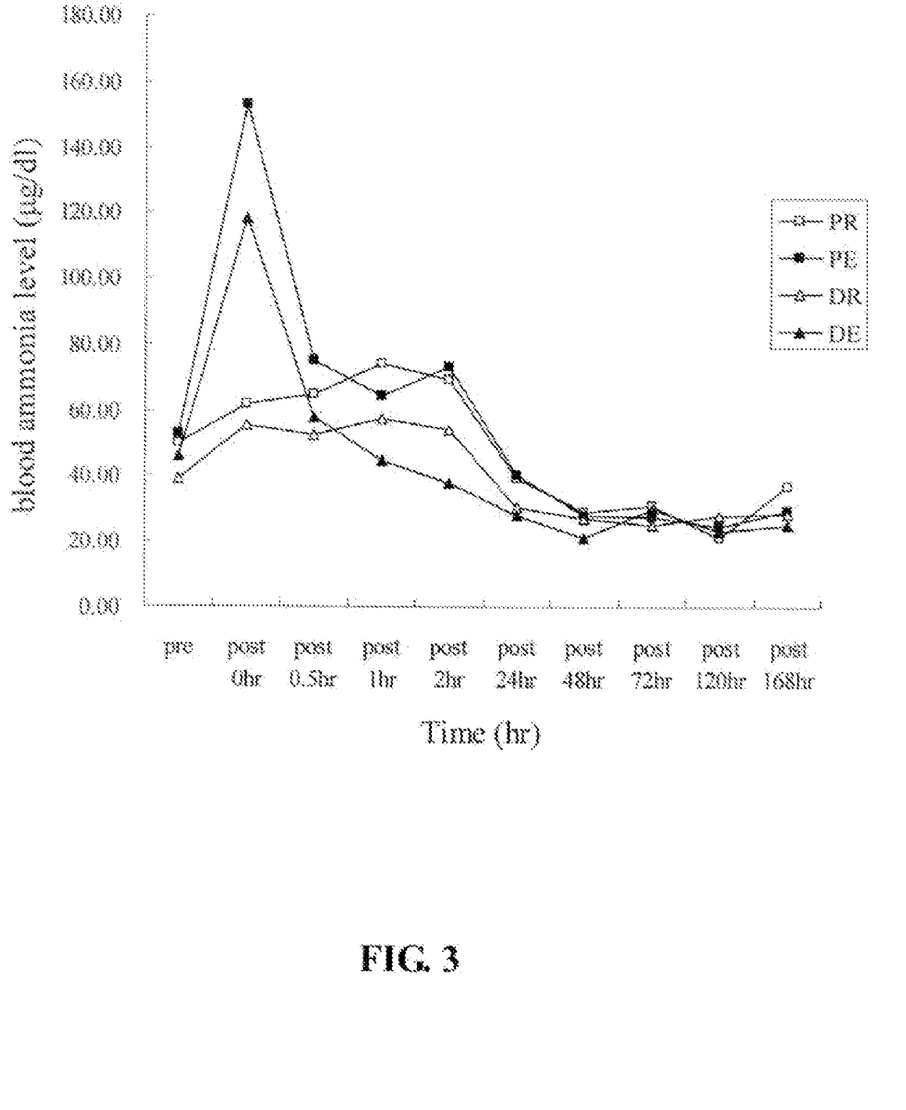
FIG. 3. The blood ammonia levels in each time point of the subjects supplemented with placebo or cyclohexenone of *Antrodia camphorata* before or after exercise. □:the relax group receiving placebo (PR), ▓he exercise group receiving placebo (PE), Δ: the relax group receiving cyclohexenone of *Antrodia camphorata* (DR), ▲: the exercise group receiving cyclohexenone of *Antrodia camphorata* (DE).

From the results of Table 4 and FIG. 3, the blood ammonia levels in the PE group and the DE group after high intensity exhausted exercise at 80% $VO_2$max were significantly higher than those in the PR group and in the DR group (p>0.05). The blood ammonia levels of PE group and DE group at 1 h post exercise would gradually recover and showed no significant different (p>0.05) to the before-exercise values. While the blood ammonia levels showed significant difference (p<0.05) between DE group and PE group at 2 h post exercise. In addition, the ammonia levels were significantly lower in DE group at 24 h post exercise than those before exercise while no such phenomenon was observed in the PE group at the same time points. Therefore supplementation of cyclohexenone from *Antrodia camphorata* after exercise facilitates the metabolism of blood ammonia, which promotes the metabolism of blood ammonia and further delaying the fatigue caused by exhaustive exercise.

(4) Analysis Of Lactate Levels In Blood

Lactate is the metabolic product of anaerobic glycolysis from glycogen and glucose in muscle and liver. In quiet state, less lactate is produced. The hyopxia is more obvious during long-term or intense exercise, with the anaerobic metabolism accelerated. Lactate accumulation is increased in muscle when rate of lactate synthesis is higher than that of lactate oxidation in mitochondria. Accumulation of lactate results in high levels of hydrogen ions, and the lowering of the pH. The activity of phosphofructokinase will be inhibited, thus decrease glycosylation and ATP re-synthesis. Alternatively, the addition of hydrogen ions affects calcium ions release from sarcoplasmic reticulum and decreases the contractibility of muscle fibers. Lactate is therefore used as an index for fatigue.

The measurement of blood lactate was performed with an automated blood analyzer using dry chemistry method (Johnson & Johnson DT-60II) based on enzyme function and spectrophotometric theory. Lactate oxidase was added into a defined amount of plasma for reaction, followed by addition of 4-aminoantipyrine and 1,7-dihydroxynaphthalene. A red product was formed through activities of peroxidase. The reactions are shown below:

The absorbance at 540 nm was measured to obtain the concentration of blood lactate. Results are shown in Table 5 and FIG. 4.

TABLE 5

The blood lactate levels (mmol/l) of the subjects supplemented with placebo or cyclohexenone of *Antrodia camphorata* before or after excercise.

| Group | Prior to exercise | Post-exercise 0 h | Post-exercise 0.5 h | Post-exercise 1 h | Post-exercise 2 h | Post-exercise 24 h | Post-exercise 48 h | Post-exercise 72 h | Post-exercise 120 h | Post-exercise 168 h |
|---|---|---|---|---|---|---|---|---|---|---|
| Placebo | | | | | | | | | | |
| Relax (PR) | 2.43 ± 0.12 | 2.62 ± 0.11 | 2.80 ± 0.19 | 2.50 ± 0.17 | 2.43 ± 0.14 | 2.71 ± 0.20 | 2.41 ± 0.12 | 2.15 ± 0.21 | 2.30 ± 0.17 | 2.68 ± 0.12$^{bd}$ |
| exercise (PE) | 2.68 ± 0.17 | 7.79 ± 0.80*$^{ac}$ | 3.45 ± 0.28*$^c$ | 2.64 ± 0.23 | 2.68 ± 0.13 | 2.69 ± 0.16 | 2.45 ± 0.21 | 2.17 ± 0.19* | 2.27 ± 0.17* | 2.09 ± 0.14* |
| cyclohexenone | | | | | | | | | | |
| Relax (DR) | 2.54 ± 0.18 | 2.39 ± 0.19 | 2.25 ± 0.19* | 3.00 ± 0.53 | 2.52 ± 0.20 | 2.26 ± 0.16 | 2.71 ± 0.12 | 2.22 ± 0.18 | 2.41 ± 0.30 | 2.41 ± 0.19 |
| exercise (DE) | 2.50 ± 0.17 | 7.07 ± 0.97*$^{ac}$ | 3.20 ± 0.31*$^c$ | 2.96 ± 0.18 | 2.9 ± 0.15 | 2.39 ± 0.20 | 2.77 ± 0.20 | 2.18 ± 0.19 | 2.53 ± 0.25 | 2.23 ± 0.16 | n = 15, values are presented as (Mean ± SEM).
*represents p < .05, significant difference from the previous test;
$^a$represents p < .05, significant larger than that of the same time point in the PR group;
$^b$represents p < .05, significant higher than that of the same time point in the PE group;
$^c$represents p < .05, significant higher than that of the same time point in the DR group;
$^d$represents p < .05, significant higher than that of the same time point in the DE group.

Figure 4:
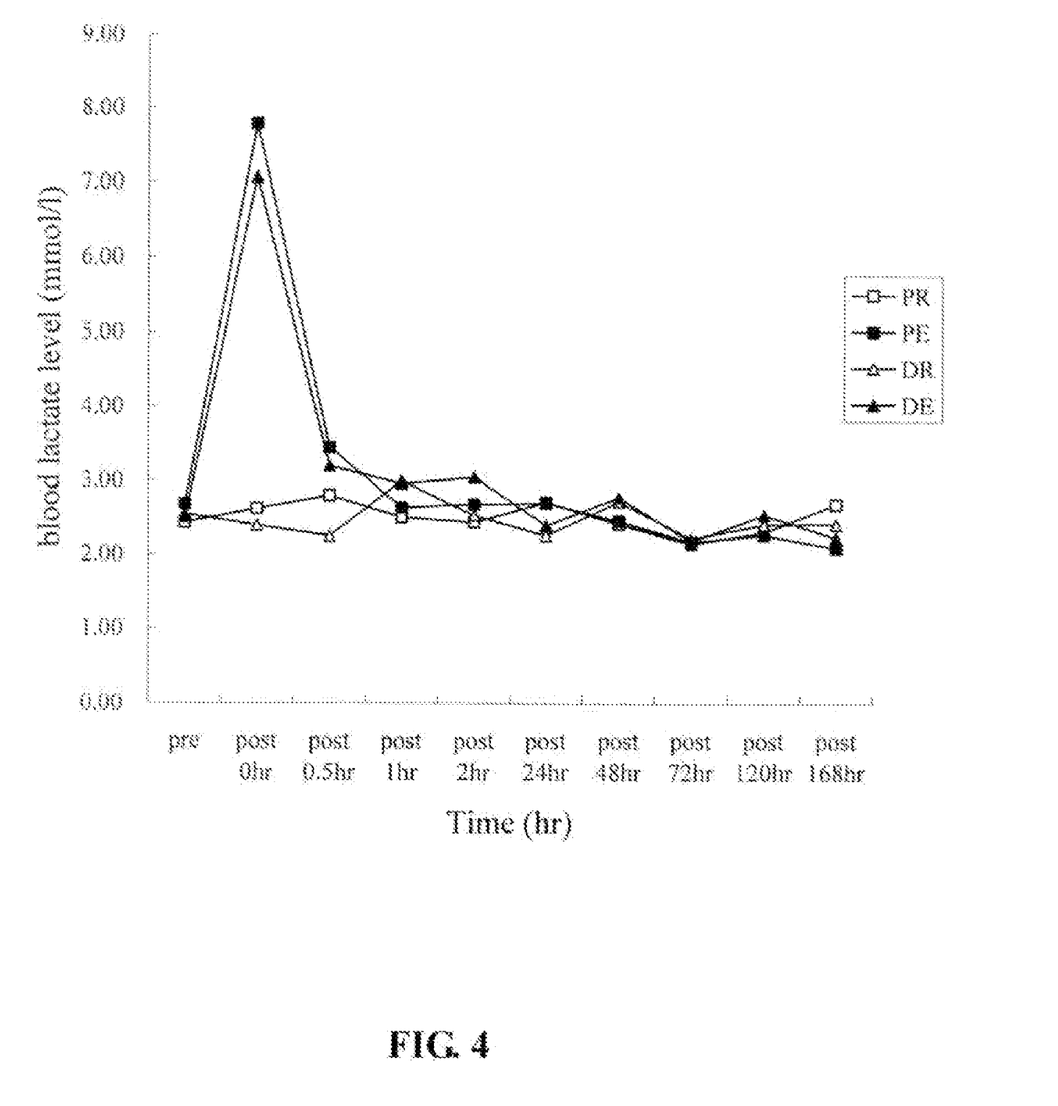
FIG. 4. The blood lactate levels in each time point of the subjects supplemented with placebo or cyclohexenone of *Antrodia camphorata* before or after exercise. □: the relax group receiving placebo (PR), ▓ the exercise group receiving placebo (PE), Δ: the relax group receiving cyclohexenone of *Antrodia camphorata* (DR, ▲: the exercise group receiving cyclohexenone of *Antrodia camphorata* (DE).

From the results of Table 5 and FIG. 4, the blood lactate levels in the PE group and the DE group after high intensity exhausted exercise at 80% $VO_2$max were significantly higher (p<0.05) than those in the PR group and in the DR group within 0.5 h. The introduction of exercise intensity in blood lactate levels of two exercise groups (i.e. PE group and DE group) is significantly different from those of non-exercise groups (i.e. PR groups and DR group). The blood lactate levels of PE group and DE group at 1 h post exercise would gradually recover and near the quiet values before exercise and showed no significant difference (p>0.05) to the before-exercise values. Therefore supplementation of cyclohexenone from *Antrodia camphorata* after exercise did not affect the metabolism of blood lactate.

(5) Analysis Of Free Fatty Acid Levels

Free fatty acids are derived from the lipolysis of adipose tissue in muscle fibers or hydroylzed from triacylglycerols in cells. Glycogen stored in muscle would be depleted during endurance exercise. Glycogenolysis decreases with the increase of time during exercise, and fatty acids take over as energy source. This is associated with a decrease in ATP production and followed by generation of fatigue. Besides, the competition of free fatty acids in the binding of tryptophan to albumin causes the increase of free tryptophan in blood. Tryptophan is a precursor to serotonin. The synthesis of serotonin is increased when tryptophan enters brain. Increase in brain serotonin levels leads malfunction on some parts of central system, such as reduction of dopamine activity, which also causes the generation of fatigue and promotes sleep. Therefore, free fatty acid levels can be applied as an index for lipolysis and fatigue.

The measurement of free fatty acid level was performed based on enzyme function and spectrophotometric theory. Acyl CoA synthetase and acyl CoA oxidase were added into a defined amount of plasma for reaction. A purple product was formed through activities of peroxidase. The reactions are shown below:

4-AAP; 4-aminoantipyrine

TOOS: N-ethyl-N-(2-hydroxy-3-sulphopropyl) m-toludine

The absorbance at 550 nm was measured to obtain the concentration of free fatty acid. Results are shown in Table 6 and FIG. 5.

TABLE 6

The levels (μmol/l) of free fatty acid in the subjects supplemented with placebo or cyclohexenone of *Antrodia camphorata* before or after excercise.

| Group | Prior to exercise | Post-exercise 0 h | Post-exercise 0.5 h | Post-exercise 1 h | Post-exercise 2 h | Post-exercise 24 h | Post-exercise 48 h | Post-exercise 72 h | Post-exercise 120 h | Post-exercise 168 h |
|---|---|---|---|---|---|---|---|---|---|---|
| Placebo | | | | | | | | | | |
| Relax | 0.33 ± | 0.26 ± | 0.31 ± | 0.28 ± | 0.30 ± | 0.37 ± | 0.38 ± | 0.32 ± | 0.29 ± | 0.27 ± |
| (PR) | 0.04 | *0.03 | 0.04 | 0.04 | 0.05 | 0.05 | 0.04 | 0.03 | 0.03 | 0.04 |
| exercise | 0.35 ± | 0.94 ± | 0.61 ± | 0.62 ± | 0.63 ± | 0.47 ± | 0.39 ± | 0.47 ± | 0.47 ± | 0.40 ± |
| (PE) | 0.05 | 0.12*ac | 0.08*ac | 0.11*ac | 0.08*ac | 0.06c | 0.05 | 0.06ac | 0.05 | 0.06 |
| cyclohexenone | | | | | | | | | | |
| Relax | 0.38 ± | 0.33 ± | 0.34 ± | 0.30 ± | 0.23 ± | 0.28 ± | 0.29 ± | 0.31 ± | 0.48 ± | 0.28 ± |
| (DR) | 0.04 | 0.04 | 0.04* | 0.05 | 0.03* | 0.05 | 0.04 | 0.05 | 0.10a | 0.03 |
| exercise | 0.34 ± | 0.91 ± | 0.60 ± | 0.61 ± | 0.59 ± | 0.41 ± | 0.28 ± | 0.44 ± | 0.30 ± | 0.32 ± |
| (DE) | 0.03 | 0.14*ac | 0.08*ac | 0.09*ac | 0.08*ac | 0.06c | 0.04 | 0.05c | 0.04 | 0.06 | n = 15, values are presented as (Mean ± SEM).

*represents p < .05, significant difference from the previous test;

a represents p < .05, significant larger than that of the same time point in the PR group;

b represents p < .05, significant higher than that of the same time point in the PE group;

c represents p < .05, significant higher than that of the same time point in the DR group;

d represents p < .05, significant higher than that of the same time point in the DE group.

Figure 5:
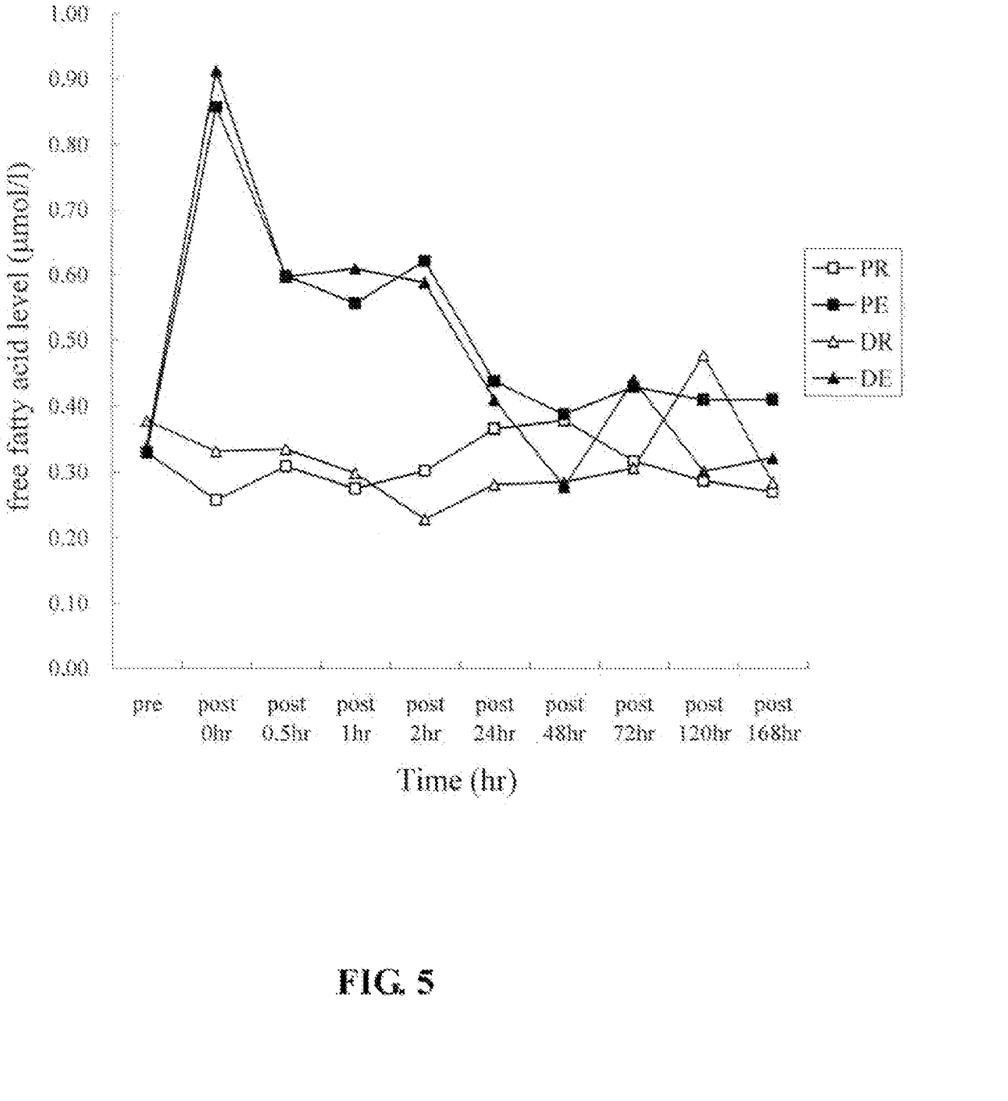
FIG. 5. The free fatty acid levels in each time point of the subjects supplemented with placebo or cyclohexenone of *Antrodia camphorata* before or after exercise, □: the relax group receiving placebo (PR), ▓ the exercise group receiving placebo (PE), Δ: the relax group receiving cyclohexenone of *Antrodia camphorata* (DR). ▲: the exercise group receiving cyclohexenone of *Antrodia camphorata* (DE).

From the results of Table 6 and FIG. 5, the levels of free fatty acid in the PE group and the DE group at 2 h post high intensity exhausted exercise at 80% $VO_2$max were significantly higher (p<0.05) than those in the PR group and in the DR group. The blood free fatty acid levels of PE group and DE group at each time point after exercise showed no significant difference (p>0.05) to each other. Therefore supplementation of cyclohexenone from *Antrodia camphorata* after exercise did not affect the metabolism of free fatty acid.

In summary, the creatine phosphate kinase levels increased right away but recovered to the level before-exercise within 0.5 h when immediate supplemented with cyclohexenone of *Antrodia camphorata* after high intensity exhausted exercise at 80% $VO_2$max. This shows that immediate supplementation of cyclohexenone from *Antrodia camphorata* has significant effect (p<0.05) in metabolism of creatine phosphate kinase after exhausted exercise. The blood ammonia level in the exercise group receiving cyclohexenone from *Antrodia camphorata* was significantly superior to that of the relax group receiving cyclohexenone of *Antrodia camphorata* post exercise at 2 h (p<0.05). Besides, the fatigue indexes such as blood glucose, blood lactate and free fatty acid showed no significant difference between the exercise groups receiving placebo or receiving cyclohexenone of *Antrodia camphorata* respectively. Therefore, immediate supplementation of cyclohexenone from *Antrodia camphorea* after high intensity exhausted exercise at 80% $VO_2$max is beneficial to the recovery of creatine phosphate kinase and blood ammonia, further delays physiological fatigue.

What is claimed is:

1. A method for delaying physiological fatigue which comprises administering to a subject in need thereof an effective amount of a cyclohexenone compound of *Antrodia camphorata* having the following formula:

wherein X and Y is oxygen or sulfur, $R_1$, $R_2$ and $R_3$ are each a hydrogen atom, methyl or $(CH_2)_m CH_3$, and m=1-12; n=1-12.

2. The method as claimed in claim 1, wherein the cyclohexenone compound is isolated from the organic solvent extracts of *Antrodia camphorata*.

3. The method as claimed in claim 2, wherein the organic solvents are selected from the group consisting of alcohols, esters, alkanes, and halogenated alkanes.

4. The method as claimed in claim 3, wherein the alcohol is ethanol.

5. The method as claimed in claim 1, wherein the cyclohexenone compound is isolated from the aqueous extracts of *Antrodia camphorata*.

6. The method as claimed in claim 1, wherein the cyclohexenone compound is 4-hydroxy-2,3-dimethoxy-6-methyl-5(3,7,11-trimethyl-dodeca-2,6,10-trienyl)-cyclohex-2-enone.

7. The method as claimed in claim 1, wherein the cyclohexenone compound has an anti-fatigue function based on promotion of the metabolism of creatine phosphate kinase after exercise.

8. The method as claimed in claim 7, wherein the exercise is a high intensity exhaustive exercise at 80% $VO_2$max.

9. The method as claimed in claim 6, wherein the cyclohexenone compound has an anti-fatigue function based on promotion of the metabolism of creatine phosphate kinase after exercise.

10. The method as claimed in claim 9, wherein the exercise is a high intensity exhaustive exercise at 80% $VO_2$max.

11. The method as claimed in claim 1, wherein the cyclohexenone compound has an anti-fatigue function based on promotion of the metabolism of blood ammonia after exercise.

12. The method as claimed in claim 11, wherein the exercise is a high intensity exhaustive exercise at 80% $VO_2$max.

13. The method as claimed in claim 6, wherein the cyclohexenone compound has an anti-fatigue function based on promotion of the metabolism of blood ammonia after exercise.

14. The method as claimed in claim 13, wherein the exercise is a high intensity exhaustive exercise at 80% $VO_2$max.

* * * * *

UNITED STATES PATENT AND TRADEMARK OFFICE
CERTIFICATE OF CORRECTION

PATENT NO. : 7,468,392 B1
APPLICATION NO. : 11/829745
DATED : December 23, 2008
INVENTOR(S) : Sheng-Yun Liu et al.

Page 1 of 1

It is certified that error appears in the above-identified patent and that said Letters Patent is hereby corrected as shown below:

At column 2, lines 33-44, Formula (1) should be corrected to:

(1)

In Claim 1, at column 17, lines 35-45, the formula should be corrected to:

Signed and Sealed this
Twenty-fourth Day of April, 2012

David J. Kappos
*Director of the United States Patent and Trademark Office*